United States Patent
Choi (10) Patent No.: US 6,458,132 B2
(45) Date of Patent: Oct. 1, 2002

(54) SPINE SUPPORTING SYSTEM

(75) Inventor: Gil-Woon Choi, Suit 103-1111, Sidae-yonsu Apt., Cheonghak-dong 451, Yonsu-ku, Inchon-city, 406-120 (KR)

(73) Assignees: Gil-Woon Choi (KR); Chun-Tek Lee (KR)

( * ) Notice: Subject to any disclaimer, the term of this patent is extended or adjusted under 35 U.S.C. 154(b) by 0 days.

(21) Appl. No.: 09/777,808

(22) Filed: Feb. 5, 2001

(30) Foreign Application Priority Data

Mar. 15, 2000 (KR) .......................................... 2000-7403

(51) Int. Cl.[7] .............................................. A61B 17/56
(52) U.S. Cl. .......................................... 606/61; 606/72
(58) Field of Search .............................. 606/61, 72, 73, 606/53, 60, 86

(56) References Cited

U.S. PATENT DOCUMENTS

| | | |
|---|---|---|
| 4,611,580 A | 9/1986 | Wu |
| 5,129,388 A | 7/1992 | Vignaud et al. |
| 5,176,680 A | 1/1993 | Vignaud et al. |
| 5,217,497 A * | 6/1993 | Mehdian ...................... 606/61 |
| 5,261,912 A * | 11/1993 | Frigg .......................... 606/61 |
| 5,385,583 A * | 1/1995 | Cotrel ......................... 606/61 |
| 5,443,467 A | 8/1995 | Biedermann et al. |
| 5,520,689 A * | 5/1996 | Schlapfer et al. ............. 606/61 |
| 5,536,268 A * | 7/1996 | Griss .......................... 606/61 |
| 5,725,527 A * | 3/1998 | Biedermann et al. ......... 606/61 |
| 5,782,833 A * | 7/1998 | Haider ........................ 606/61 |
| 6,077,262 A * | 6/2000 | Schlapfer et al. ............. 606/61 |
| 6,251,112 B1 * | 6/2001 | Jackson ....................... 606/61 |

* cited by examiner

Primary Examiner—Pedro Philogene
(74) Attorney, Agent, or Firm—Mathews, Collins, Shepherd & McKay, P.A.

(57) ABSTRACT

The present invention is a spine supporting system where a screw, with a head having an interior female thread, is attached to the spine. An interior bolt is temporarily held by the interior female threads of the outer cap, where the outer cap aligns the inner bolt with the interior female threads of the screw. The inner bolt attaches to the interior threads of the screw and the outer cap secures a support rod to the screw. The present invention allows the support rod to be secured to the screw in one step, using a single tool during an operation.

6 Claims, 13 Drawing Sheets

FIG.1

--PRIOR ART--

FIG. 2

--PRIOR ART--

FIG.3

--PRIOR ART--

FIG.4

--PRIOR ART--

SPINE SUPPORTING SYSTEM

BACKGROUND OF THE INVENTION

1. Field of the Invention

The present invention relates to a spine supporting system for correcting or fixing a spine to be a stable state at a diseased part in spine operation.

2. Background of the Related Art

Generally, a spinal column (referred to as a 'spine' in the followings) of a normal human body standing erectly appears to be a straight line in front view and 'Lasy-S' curved in side view. That is, the thoracic spine has a shape gently bent backwardly in side view, while the cervical spine and the lumber spine has a shape bent forwardly.

In the human body, the spine forms a curve of 'Lasy-S' by connecting a plurality of bodies of spine with a disk, one section of the spine consists of cylindrical body and the arch located backward, the posterior spinal arch comprises a spinal canal with a pair of pedicles, superior or inferior facets extending backwardly from the pedicles, laminas and a spinous process, and a nerve is located through the spinal canal.

In such a spine, when the disk connecting the body is degenerated and ruptured so that it is separated from regular position or a joint consist of a rear projection of the spine is damaged and degenerated, and when the external force is loaded to or press the nerve passing through the spinal canal with various reasons such that the spine has a deformity and displacement from the normal position, it is known that pains are caused.

Therefore, since the pain are occurred continuously when the spine is in unstable state as mentioned above, the diseased part of the spine should be decompressed in order to kill the pains, and an operation correcting or fixing a spine to be a stable state, is required due to the unstable state of the spine in decompressing.

Namely, in case of a patient of which a part of the spine is broken or damaged, a corresponding spine or adjacent spine is supported through an operation using the spine supporting system. The spine supporting system used in this case, comprises a screw inserted to the damaged or adjacent upper and lower spinal pedicle of the spine as a supporting structure, a rod inserted in each of the screw, and a inner bolt and outer cap for fixing the rod to the screw.

Figure 1:
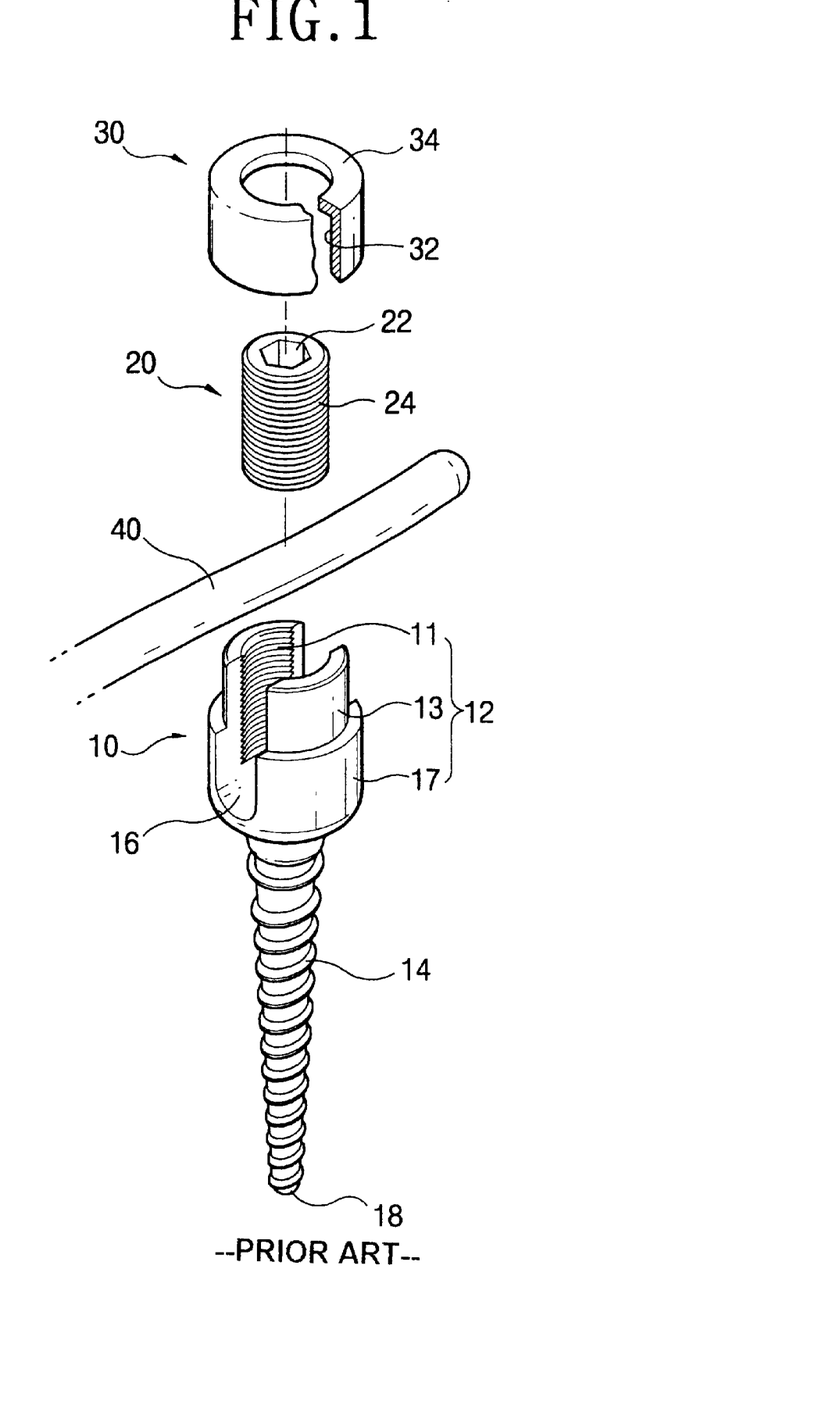
FIG. 1 is an exploded perspective view showing a structure of a spine supporting system according to the prior art.
Figure 2:
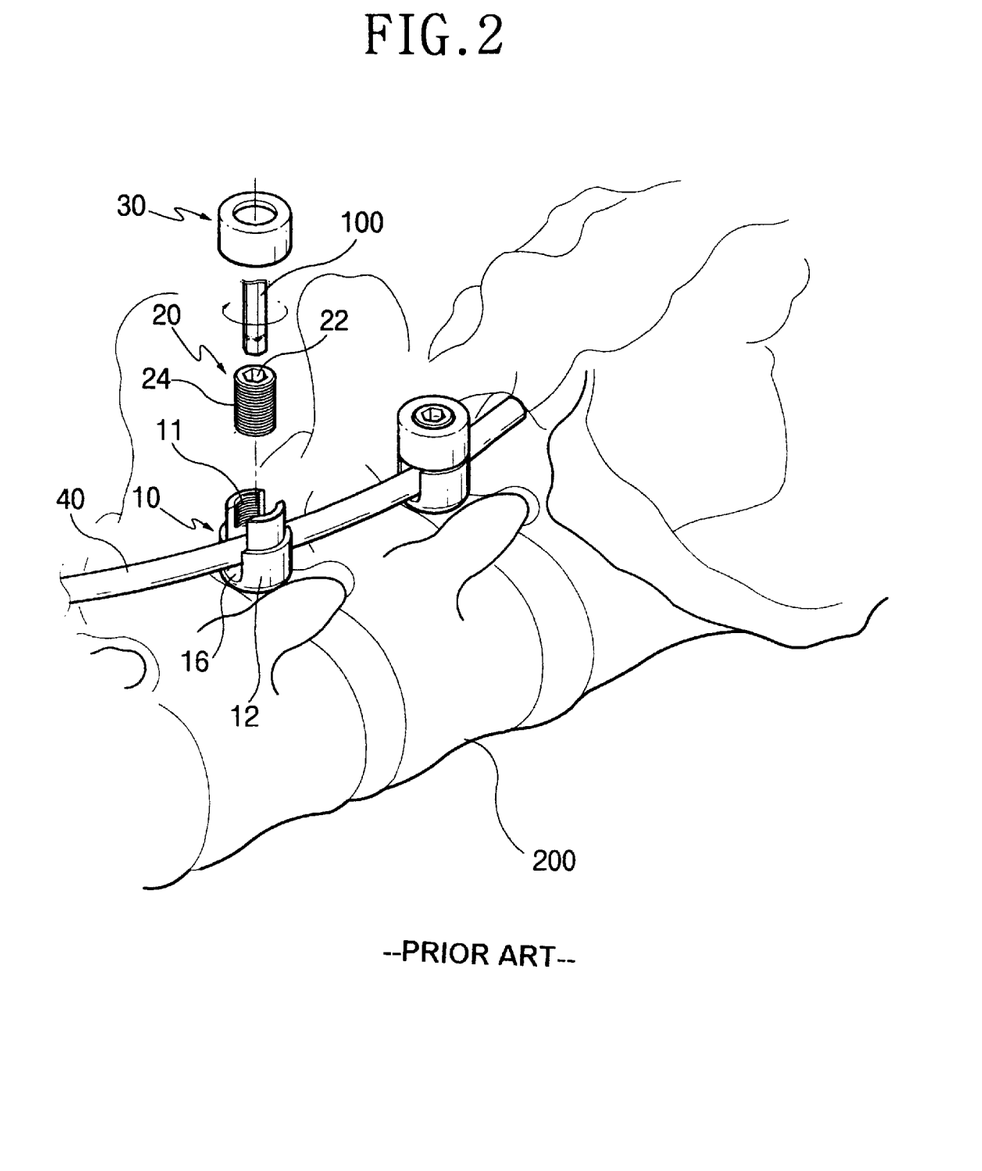
FIG. 2 is a perspective view showing an operation process by a spine supporting system of the prior art.
Figure 3:
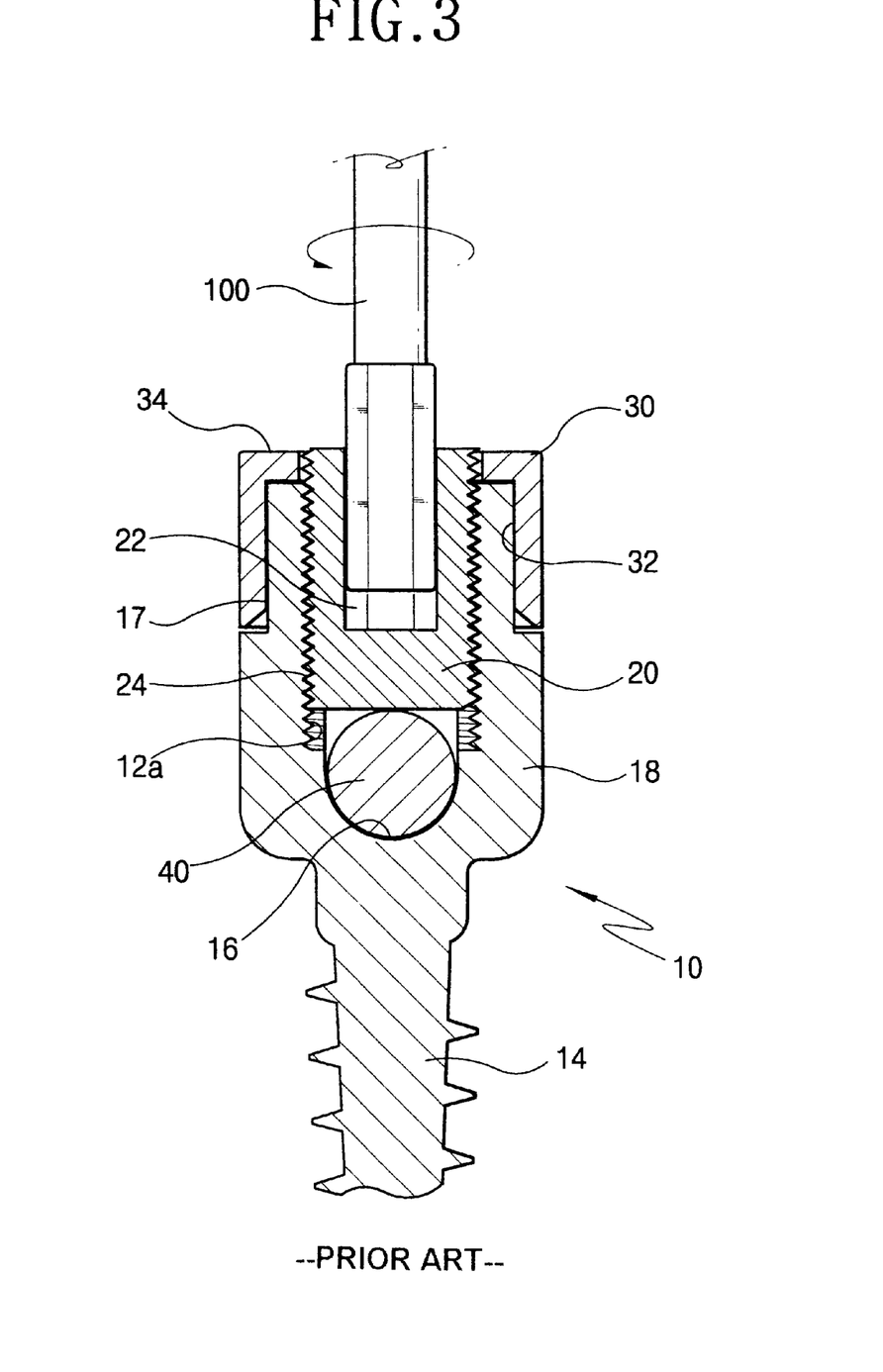
FIG. 3 is a sectional view showing an operation state by a spine supporting system of the prior art.
Figure 4:
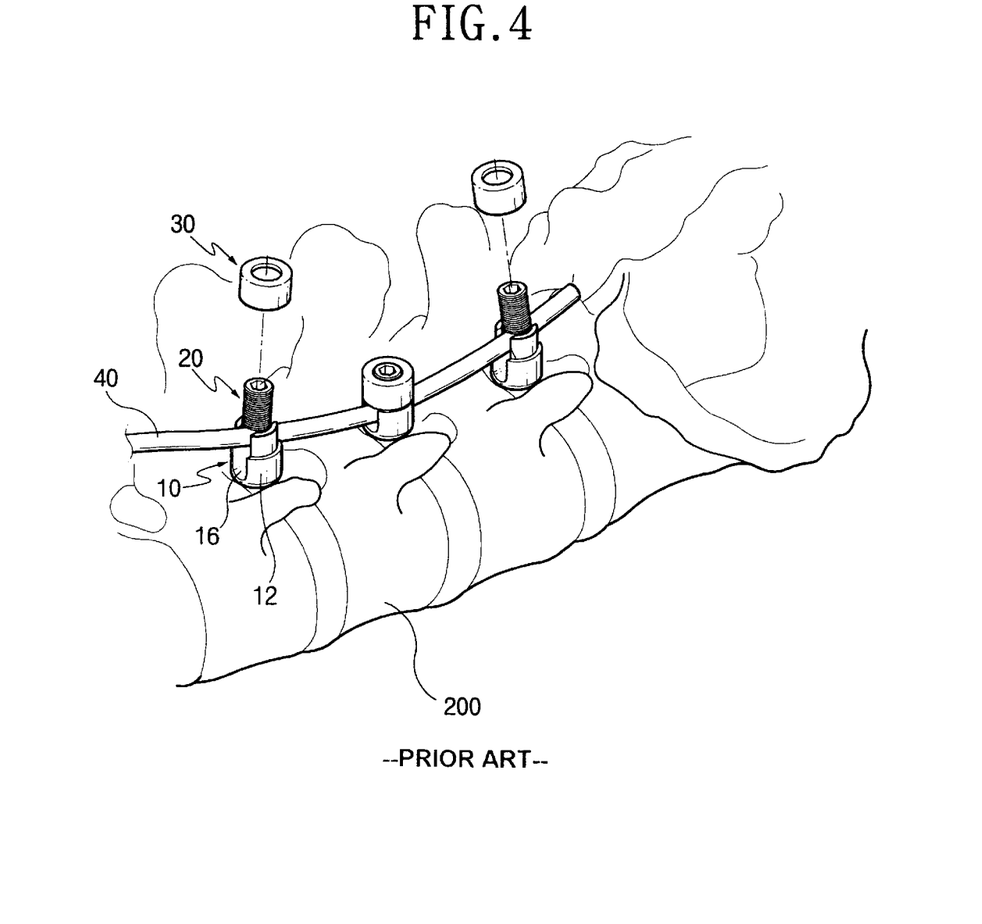
FIG. 4 is a perspective view for describing difficulties of an operation by a spine supporting system of the prior art.

Referring to FIG. 1–FIG. 3, the spine supporting system according to the prior art will be explained roughly. FIG. 1 is an exploded perspective view showing a structure of a spine supporting system according to the prior art, FIG. 2 is a perspective view showing an operation process by a spine supporting system of the prior art, FIG. 3 is a sectional view showing an operation state by a spine supporting system of the prior art, and FIG. 4 is a perspective view for describing difficulties of an operation by a spine supporting system of the prior art.

In these figures, a reference numeral 10 is a screw having a head 12 and a body 14 formed to be integrated with a lower part of the head 12, a reference numeral 20 is an inner bolt screwed in the head 12 of the screw 10, a reference numeral 30 is an outer cap for improving the holding force of the inner bolt 20 by covering the head 12 of the screw 10, and a reference numeral 40 is a rod inserted in the head 12 of the screw 10 to connecting the screws 10 each other.

The head 12 of the screw 10 could be described divided into an inner structure and outer structure. The inner structure of the head 12 includes a female thread 11 for the inner bolt 20 and 'U' shaped groove 16 for passing and fixing the rod 40 which connects the spine supporting system described below, and the outer structure of the head 12 includes a cap-assembled surface 13 covered with the outer cap 30 to prevent the decrease of strength in the head 12 due to the formation of the groove 16 and to increase the fixation and a head block 17 formed at an lower part of a cap-assembled surface 13 and connected with the body 14.

The body 14 of the screw 10 has a lengthy cone shape and is formed at a circumference thereof with a male thread, and an upper part thereof is integrated with the lower part of the head 12. And, a point 18 for the insertion to the spine is formed at a lower end of the body 14.

The upper surface of the inner bolt 20 is formed with a tool insertion hole 22 in which assembling tool is inserted and along with a whole circumference, a male thread 24 joined with the female thread 11 is formed.

The outer cap 30 includes an inner cavity 32 assembled with the cap assembled surface 17 and an upper surface 34 formed perpendicularly relative to the length direction.

The rod 40 has a diameter so as to be inserted in the groove 16 of the screw 16.

The function of the spine supporting system according to the prior art will be described referring to the FIG. 2 and FIG. 3. Firstly, describing the general operation procedure briefly, with incision and opening a skin of the operated part, the position in which the screw is inserted normal to the pedicle of the corresponding spine, is indicated, and then a hole is formed with a drill and the like. (Drilling Procedure)

A tapping matching a pitch of the spine supporting system, is performed at the drilling hole and the spine supporting system(specifically, the body 14) is driven in the spine with the tool 100 and so on. Then, when the required number of screw 10 is screwed to be fixed in the pedicle of the spine 200 as described above, the rod 40 which is bent suitable for the curvature of the spine, is inserted in the groove 16. Subsequently, the inner bolt 20 set in the female thread 12a is rotated several times with the tool 100 so that the rod 40 is preliminarily fixed. After the outer cap 30 covers the cap assembled surface 13 of the head 12, the rod 40 is fixed in the screw 10 rigidly by joining the inner bolt 20 tightly and the skin is sutured to complete the spine operation.

Therefore, as shown in FIG. 2, it is known that in the state the body 14 is fixed rigidly in the spine of the patient, the rod 40 is fixed rigidly in the groove 16, and further in the inner bolt 20 and screw 10, it is said that the fixation of the head 12 is stronger by the outer cap 30.

However, in the operation by the spine supporting system according to the prior art, the following defects and problems are occurring.

1. The difficulties in the insertion of the outer cap 30 and the initial setting of the inner bolt 20.

In the spine operation using the spine supporting system of the prior art wherein the rod 40 is fixed in the head 12 of the screw 10 by joining the inner bolt 20 in the female thread 12a, the outer cap 30 is joined after the inner bolt 20 is joined in the female thread 11.

This joining sequence causes the following problems. In actual operation, since the incision area of the skin is adjusted as small as possible and the inner bolt 20 has a diameter only 4 mm, it is very difficult to join the small inner bolt 20 in the female thread 11 of the head 12 with initial centering in the narrow space of operation without any guide means.

On the other hand, referring to FIG. 4, according to conditions the rod 40 is not bent suitably. In this case the operation condition is worse, since the small inner bolt 20 is joined in the female thread 11 where the rod 40 is more curved upwardly in the groove 16. That is, as the inner bolt 20 could be joined unsuitably interrupted by the rod 40, the operator could be annoyed at the trial for centering in limited operation time.

According to the joining of the inner bolt 20 prior to the outer cap 30, the centering of the inner bolt 20 is not achieved easily and the rapid joining is not easy due to the sliding and pitching during inserting, and therefore the operation is difficult and hard.

In addition, although the inner bolt 20 is inserted in the female thread 11, the bulging-out effect of the cap assembled surface 13 is occurring by the strength decrease due to the groove 16 of the head 12 as the fixation of the inner bolt 20, so that the insertion of the outer cap 30 to the cap assembled surface 13, is difficult and is causing the delay of the operation.

Furthermore, when the length of the rod 40 is excessively short or long, the rod 40 bent unsuitably is not seated in the groove 16 and causes the rear part thereof to be lifted bent by elasticity itself, and thereby in joining the outer cap 30 and head 12, the lower end of the outer cap 30 is interfered with by the rod 40 so that the stable fixation could not be maintained and the use there of is more difficult. These phenomena are more significant in the insertion of the rod 40 between the fifth lumbar and the first sacrum.

Though the outer cap 30 is joined smoothly, this outer cap 30 having only functions as a container could not operate to be associated with the inner bolt 20 so that the operation is failed by so-called loosening and separation which the rigid fixation between the inner bolt 20 and outer cap 30 is lost, and therefore the early recovery is not achieved as the patient complains of the pain.

Meanwhile, it may be assumed that the difficulties as mentioned above are solved by which the inner bolt 20 is inserted in the female thread 11 after the outer cap 30 is inserted to the head 12. However, in case of the first insertion of the outer cap 30, there is no means for holding the outer cap 30, so that the separation or damage of the outer cap 30 in the insertion of the inner bolt 20. Further, since the rod 40 is often lifted upwardly in the groove 16, the lower part of the outer cap 30 is interfered with by the rod 40 and could not inserted in the head 12 stably in this state. Therefore, the spine supporting system of the prior art has an unreasonable structure to solve the problem by inserting the outer cap 30 to the head 12.

2. The screw damages due to the design error

As the spine supporting system of the prior art is not designed to be proportional ideally with regard to the screw 10 and the head 12, various problems of design due to this is caused and especially in case of the head 12 which is formed to be large excessively, the moment causing the damage is concentrated on the boundary of the head 12 and body 14. This could be the fatal defect in the spine supporting system.

3. Strength decreases and unbalanced rotation in the spine supporting system that outer cap is integrated with the inner bolt.

In the spine supporting system of the prior art that outer cap is integrated with the inner bolt (not shown), as the inner bolt is joined only supported by the segment formed at the lower part of the outer cap, precise rotation could not be obtained and the fixation strength is weak due to the support of the inner bolt only in the lower part.

Since many defects in the spine supporting system of prior structure, is an obstacle in the spine operation requiring a rapid and accurate work, the solution thereon is desperately requested in the related academic field.

The basic concept of the spine supporting system set by the inventor, is to provide the apparatus that ensures the easiness in the insertion of the outer cap and initial setting of the inner bolt and is small and also easy to use, while exerting the rigid fixation.

The easiness in use is the concept from the doctor using the spine supporting system and is the factor, which should be considered, since the value thereof is degraded if it takes long that the doctor is accustomed to it or the operation takes long, however good the apparatus could be. To obtain such a reasonable design, the design factors are divided that the factor could be modified and not modified, and the factor could be modified is researched intensively so as to maximize the function thereof.

SUMMARY OF THE INVENTION

The present invention is contemplated to solve the aforementioned problem, and it is an object of the present invention to provide a spine supporting system, which could make the insertion of an outer cap and the initial centering of an inner bolt easy, strengthen the fixation, and contribute to the extension of life in the system by enabling the insertion of an inner bolt in a head to be guided by the outer cap and having the fixation of the outer cap, inner bolt, rod, and head to be integrated with each other after joining the outer cap rather than the inner bolt to head, departing from a fixed idea in the spine operation.

It is another object of the present invention to provide the spine supporting system, which is applied suitably to that the rod is lifted excessively in the head, and which has a double structure ensuring steady and forceful rotation and supporting a head part rigidly in the spine supporting system, which the inner bolt and outer cap is integrated.

According to one aspect of the present invention to accomplish the above object, it is provided a spine supporting system comprising: a screw having a cone shaped body and a head which includes at least a female thread, cap assembled surface, and a head block; a inner bolt having a male thread at an outer circumference to be inserted and mounted in the head of the screw; an outer cap having an inner cavity to cover the head of the screw; a rod inserted in the head of the screw and fixed by the outer cap and the inner bolt, being characterized that the outer cap is formed with a guide female thread at an upper part of an inner cavity, thereby joining the inner bolt to the guide female thread of the outer cap preliminary, and then joining the inner bolt to the female thread of the screw completely after mounting the outer cap to the head of the screw.

It is preferable that inner bolt is formed with a head part extending outwardly from an upper part thereof, and the outer cap is formed at an upper part of the guide female thread with a seat recess, in which the head part of the inner bolt is fastened and seated.

The inner cavity of the outer cap preferably includes a first and second step surface having different inner diameters in order to cover the cap-assembled surface and head block of the head.

It is preferable that the guide female thread is formed with a pitch with a limited number of a crest and root, which the inner bolt is only joined to the outer cap preliminarily and guided thereby such that the centering in the joining of the female thread of the screw and inner bolt is not interfered with.

It is preferable that the screw is formed with a first and second round surface at a boundary of the cap assembled surface and an upper surface, and a portion between the cap assembled surface and head block respectively, and the outer cap is formed with round surfaces at a portion between the first and second step surface, and an inner end of a lower part in the second step surface respectively.

More preferably, the outer cap is formed with a round cut part cutting a rod connected portion thereof as a semicircle with 2 mm depth to avoid the interference of outer cap insertion by the rod in the actual operation.

According to another aspect of the present invention to accomplish the above object, it is provided a spine supporting system comprising: an inner bolt formed with a respective fastening part of an upper part and fastening groove of the lower part; an outer cap formed with a supporting segment of an upper part, the supporting segment being joined rotatively with the fastening part of the inner bolt; and a reinforcement ring joined in the outer cap by tight fitting, a supporting segment in a lower part of the reinforcement ring being joined rotatively in the fastening groove of the inner bolt, wherein joining the inner bolt supported at the upper and lower part thereof by the outer cap and reinforcement ring.

In the present invention, after the small inner bolt is joined with the outer cap preliminarily in the outer circumstance of operation part, the outer cap larger than the inner bolt covers the head of the screw, and then the inner bolt guided by the outer cap is joined with the female thread. Therefore, the initial setting of the inner bolt and the female thread of the head and the insertion of the outer cap and head become very easy. Additionally, in the complete joining of the inner bolt, the inner bolt and the head of the screw joined, and the seat recess of the outer cap is fastened to the head part of the inner bolt, so that the screw, inner bolt, and outer cap are integrated and exert the rigid fixation. Further, since the lower part of the inner cavity in the outer cap is formed large and main contacting part of the outer cap and head of the screw is round, the outer cap could be inserted in the head without any difficulties. Also, when the inner bolt is rotated in the insertion of the outer cap to the head, the inner bolt is inserted accurately in the female thread of the head automatically, so that the rapid and accurate operation could be schemed. Furthermore, since the outer cap covers and supports the entire head part, the fixation is strengthened and the life of system is extended.

In the spine supporting system which the inner bolt and outer cap is integrated, since the upper and lower part of the inner bolt is supported by the double structure of the outer cap and reinforcement ring, steady and forceful rotation is ensured and the head part is supported rigidly.

BRIEF DESCRIPTION OF THE DRAWINGS

The features and advantages of the present invention will be more described specifically in the following description of preferred embodiments of the invention with reference to the accompanying drawings wherein.

DETAILED DESCRIPTION OF THE PREFERRED EMBODIMENT

Reference will now be made in detail to the first and second embodiment of the present invention, examples of which are illustrated in the accompanying drawings. In explaining the present invention, the same names and reference numerals will be given to the same components, and explanations in the same will be omitted.

The first embodiment

Figure 5:
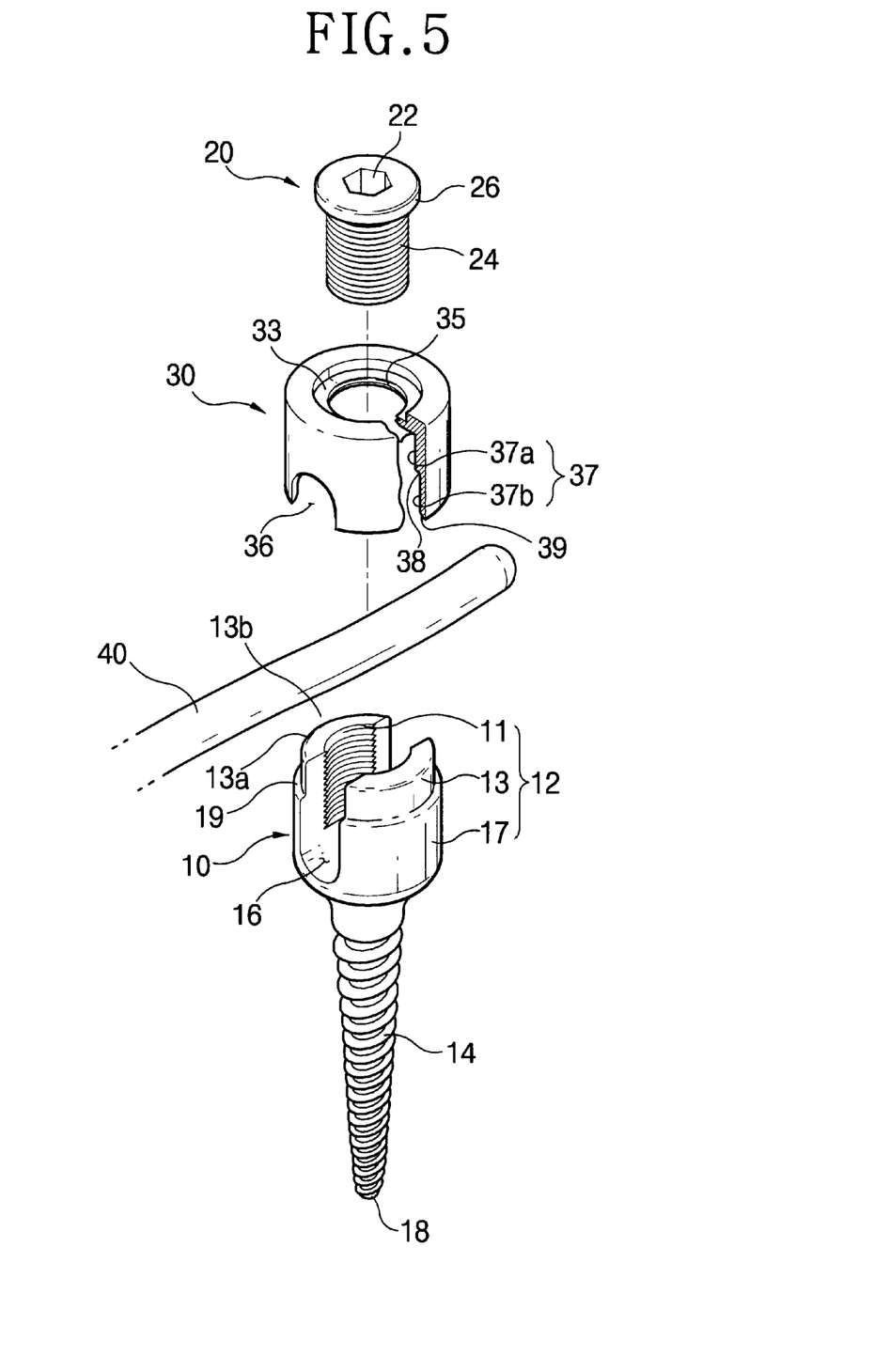
FIG. 5 is an exploded perspective view showing a structure of a spine supporting system according to the first embodiment of the present invention.
Figure 6:
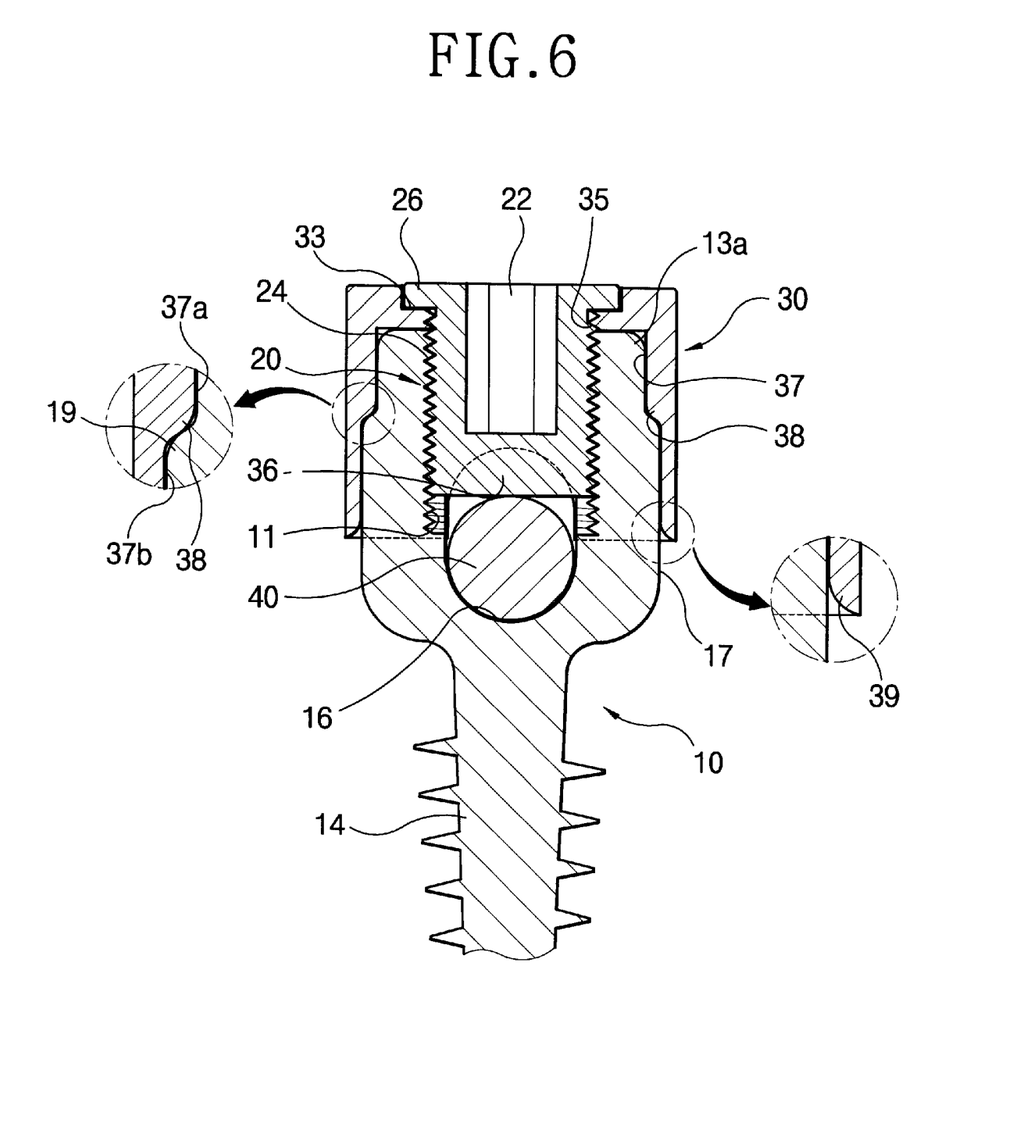
FIG. 6 is a sectional view showing a functional principle of a spine supporting system according to the first embodiment of the present invention.

The first embodiment of the present invention will be explained referring to FIG. 5 to FIG. 9. FIG. 5 is an exploded perspective view showing a structure of a spine supporting system according to the first embodiment of the present invention, and FIG. 6 is a sectional view showing a functional principle of a spine supporting system according to the first embodiment of the present invention.

Generally in the spine supporting system, a screw 10 is a rigid screw in which a body 14 is integrated with a head 12 or a polyaxial screw, which could rotates at certain angle relative to a the head 12 by forming a sphere on an upper end of a body 14. The first embodiment will be explained, with regard to the rigid screw.

In the drawings according the present embodiment the same numerals are given to the same components, and only differences to the prior art will be described in the followings.

A boundary of cap assembled surface 13 and an upper surface 13b, and a step portion between the cap assembled surface 13 and a head block 17 is formed as a round surface 13a, 19 and is strengthened so that the shearing and breakage by the external force is prevented or the insertion of an outer cap 30 is archived smoothly.

An inner bolt 20 has a head part 26, which extends and projects outwardly from an upper end thereof.

The outer cap 30 has a seat recess 33, in which the head part 26 of the inner bolt 20 could be inserted, a guide female thread 35 is formed at an inner end of the seat recess 33, and the inner bolt 20 is screwed in the guide female thread 35. The guide female thread 35 is formed to permit only 1.5 turns, i.e. 540 degrees and the inner bolt 20 is joined loosely, so that the centering is not interfered with when a female thread 11 of the screw 10 and the inner bolt 20 are joined together. That is, with this guide female thread 35, the inner bolt 20 is only joined with the outer cap 30 preliminarily.

Additionally, the outer cap 30 has a round cut part 36 of semicircle having a depth of 2 mm such that the rod 40 does not interfere with the insertion of the outer cap 30 in the operation. Also, to cover the entire head 12, i.e. the entire cap assembled surface 13 and a part of the head block 17, an inner cavity 37 comprises a first step surface 37a and a second step surface 37b. Further, to ensure the easy and smooth insertion with the round surface 13a, 19 of the head 12, a portion between the first step surface 37a and the second step surface 37b and an inner portion of the lower end is rounded.

Figure 7:
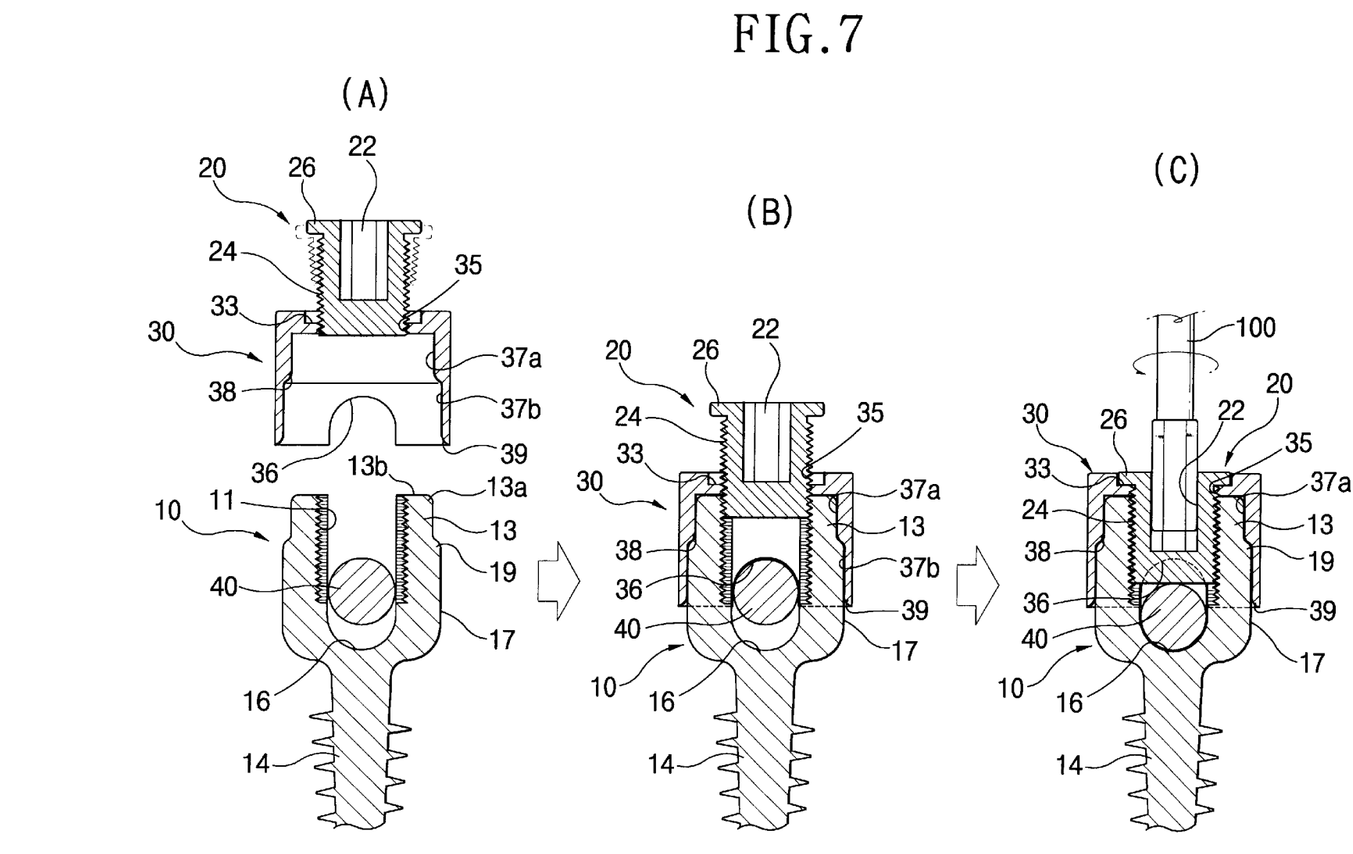
FIG. 7 is a sectional view showing an operation sequence by a spine supporting system according to the first embodiment of the present invention.
Figure 8:
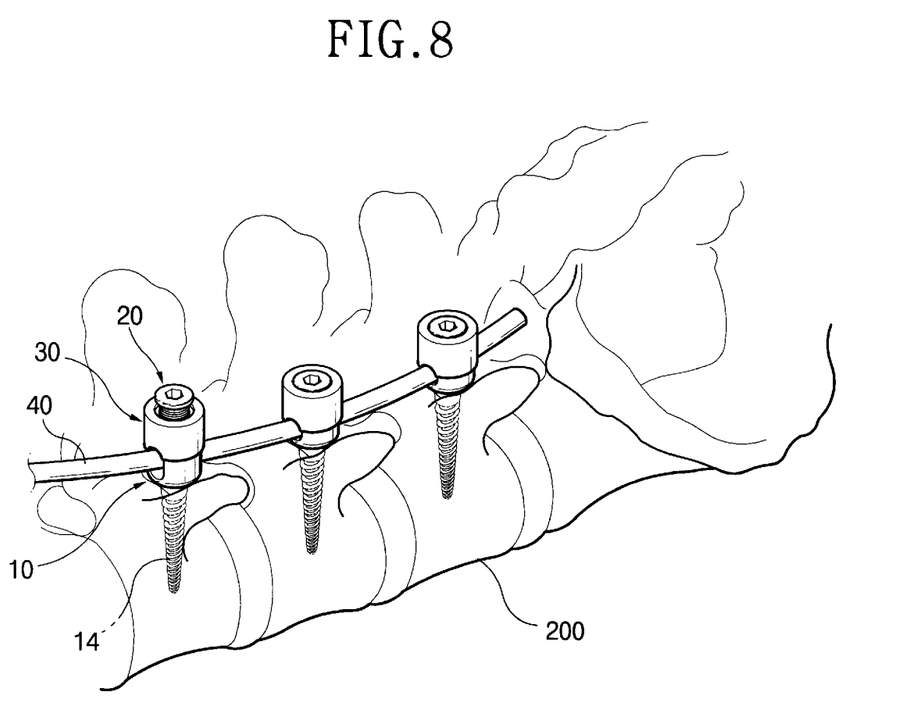
FIG. 8 is a perspective view showing an example of operation by a spine supporting system according to the first embodiment of the present invention.

The function and effectiveness of the first embodiment of the present invention will be explained referring to FIG. 7. FIG. 7 is a sectional view showing an operation sequence by a spine supporting system according to the first embodiment of the present invention, and FIG. 8 is a perspective view showing an example of operation by a spine supporting system according to the first embodiment of the present invention.

Referring to these drawings, the general operation procedure described in the above is omitted, and only the function of the mechanism according to the present embodiment will be explained in detail. Firstly as illustrated in FIG. 7(A), the rod 40 is mounted normal to be lifted slightly. In this state, the outer cap 30 of the present invention is joined with the female thread 11, and as the first step, the inner bolt 20 is joined preliminarily with the guide female thread 35. In this step, as the inner bolt 20 is caught in the guide female thread 35 by only rotation of 540 degrees, it could move to both side slightly.

This is for that no interference with regard to the centering of the inner bolt 20 to the female thread 11 occurs in a 'pre-assembling step', which the inner bolt 20 is joined with the female thread 11. More specifically, when the inner bolt 20 is only caught in the guide female thread 35 and thus simply joined with the outer cap 30 preliminarily, the centering of the inner bolt 20 center easily to the female thread 11 and the sliding and pitching during the insertion is removed such that the insertion of the inner bolt 20 is to be accurate and swift, only by mounting the outer cap 30 to the head 12 in the initial entry of the inner bolt 20.

When the preliminary joining of the inner bolt 20 and outer cap 30 is completed, the outer cap 30 is inserted to the head 12. In the insertion, with the round surface 13a, 19, the round surface 38 between the first and second step surface 37a, 37b of the inner surface of the outer cap 30, and the round surface 39 in the inner portion of the lower end of the outer cap 30, the insertion is achieved easily as follows.

In the initial insertion of the outer cap 30 to the head 12 of the screw 10, the first and second step surfaces 37a, 37b are in contact with the cap assembled surface 13 and an outer surface of the head block 17 respectively, and the round surfaces 38, 39 are in contact with the round surfaces 13a, 19 individually, and thereby the outer cap 30 is inserted to the head 12 smoothly. That is, each round surfaces 13a, 19, 38, 39 functions as an insertion guide. Also, these functions naturally and automatically as the insertion guide due to the harmony with a wider diameter and a narrower diameter.

When the outer cap 30 is completely inserted to the head 12 of the screw 10 as above, the first and second step surfaces 37a, 37b is to cover the entire cap assembled surface 13 of the head 12 and a part of the head block 17.

After the outer cap 30 is inserted to the head 12 as above, as joining the inner bolt 20 using the tool 100 as can be seen in FIG. 7(B), the inner bolt 20 guided in the outer cap 30 is joined automatically in the female thread 11 of the screw 10, and the rod 40 is inserted in the groove 16 of the screw 10 by the fixing force of the inner bolt 20. And, as the inner bolt is joined further as shown in FIG. 7(C), the bottom surface of the inner bolt 20 fixes the rod 20 in the head 12 of the screw 10 by pushing it, and at the same time the head part 26 of the inner bolt 20 is inserted and seated in the seat recess 33 of the outer cap 30.

In such a complete joining of the inner bolt 20, since the inner bolt 20 is inserted in the female thread 11 of the head 12 in the screw 10 and the head 12 covered with the head 12 maintains the integrated state which the seat recess 33 is fastened to the head part 26 of the inner bolt 20, the rod 40 is fixed in the rod 40 rigidly.

As described above, the present invention fixes the rod 40 in the screw 10 by rotating and inserting the inner bolt 20 automatically in the female thread 11 of the head 12.

Figure 9:
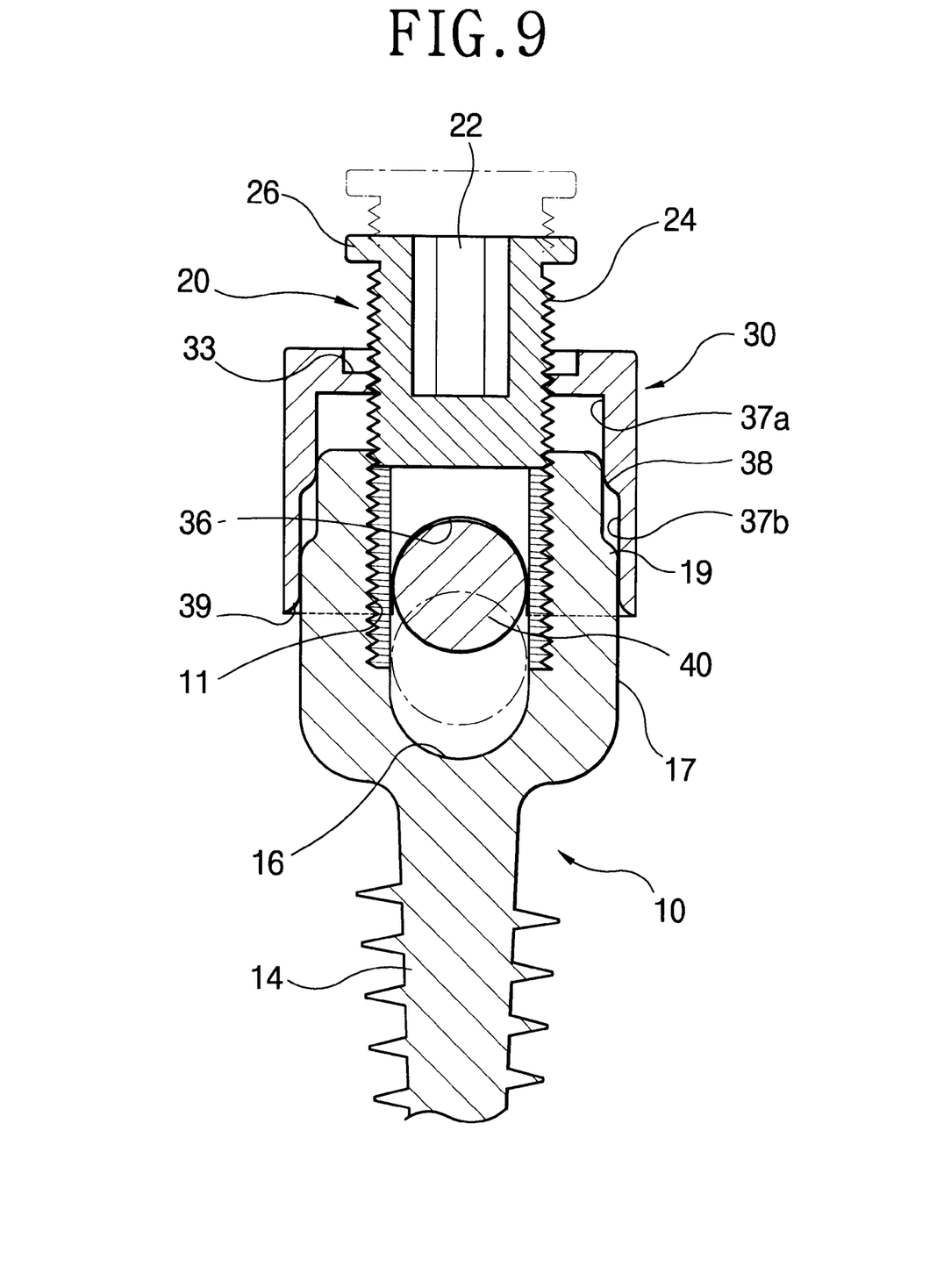
FIG. 9 is a sectional view showing another function of a spine supporting system according to the first embodiment of the present invention.

FIG. 9 is a sectional view showing another function of a spine supporting system according to the first embodiment of the present invention.

It is often a case that the actual operation is not the same as that in the textbook according to the state of the patient. FIG. 9 illustrates the state that the inner bolt 20 is joined, as the rod 40 is not mounted accurately in the groove 16, in other words the rod 40 is not in the well fitting. The rod 40 is lifted excessively to the upper part of the groove 16.

In this state, as the outer cap 30 of the present invention is inserted to the head 12, the outer cap 30 is inserted to the head 12 of the screw 10 preliminarily with the rod 40 is inserted in the round cut part 36 formed in the outer cap 30. Subsequently, as the inner bolt 20 is fastened, the inner bolt 20 guided in the outer cap 30 is joined in the female thread 11 and this inserts the outer cap 30 to the head 12, and thereby the rod 40 in the head 12 of the screw 10 is fixes as the above.

The second embodiment

Figure 10:
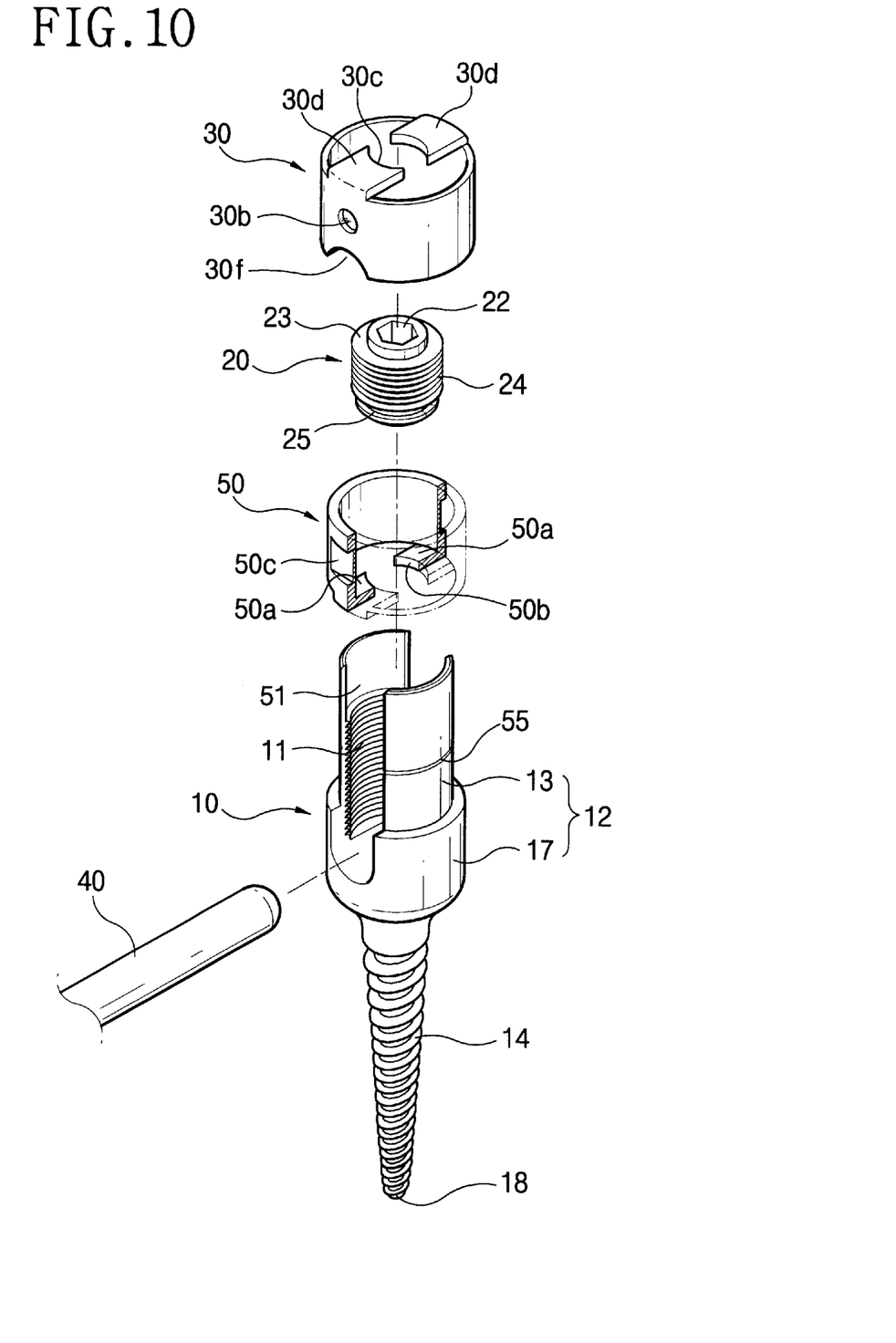
FIG. 10 is an exploded perspective view showing a structure of a spine supporting system according to the second embodiment of the present invention.
Figure 11:
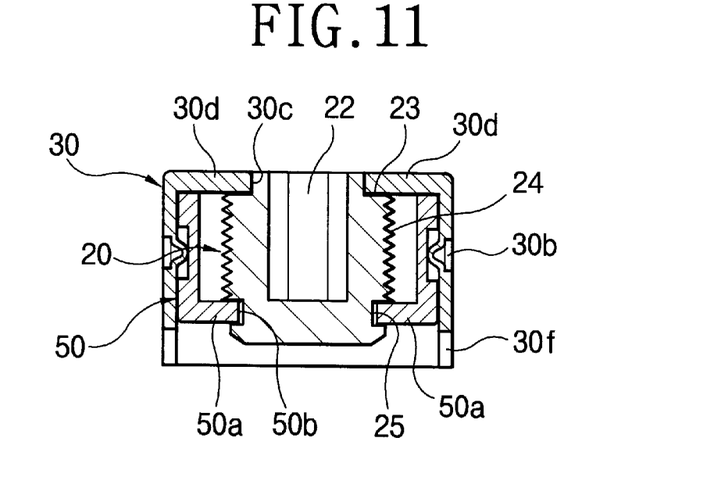
FIG. 11 is a sectional view showing a double structure of an outer cap and a reinforcement ring applied to a spine supporting system according to the second embodiment of the present invention.
Figure 12:
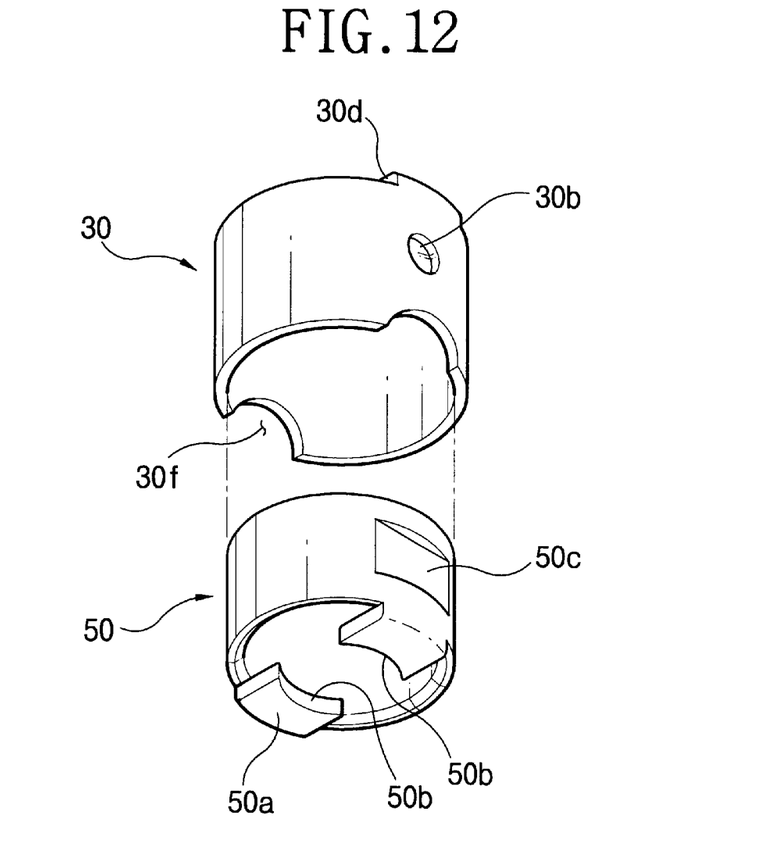
FIG. 12 is an exploded perspective view showing a double structure of an outer cap and a reinforcement ring applied to a spine supporting system according to the second embodiment of the present invention.
Figure 13:
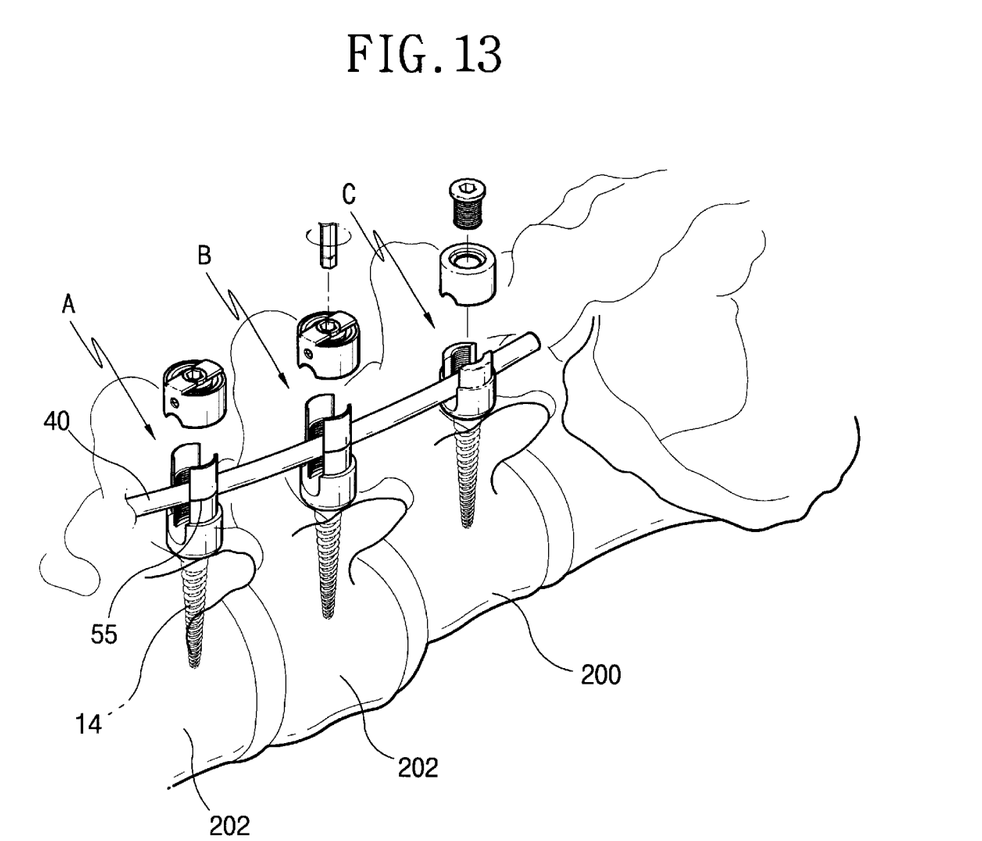
FIG. 13 is an exploded perspective view showing an example of operation using a spine supporting system according to the second embodiment of the present invention.
Figure 14:
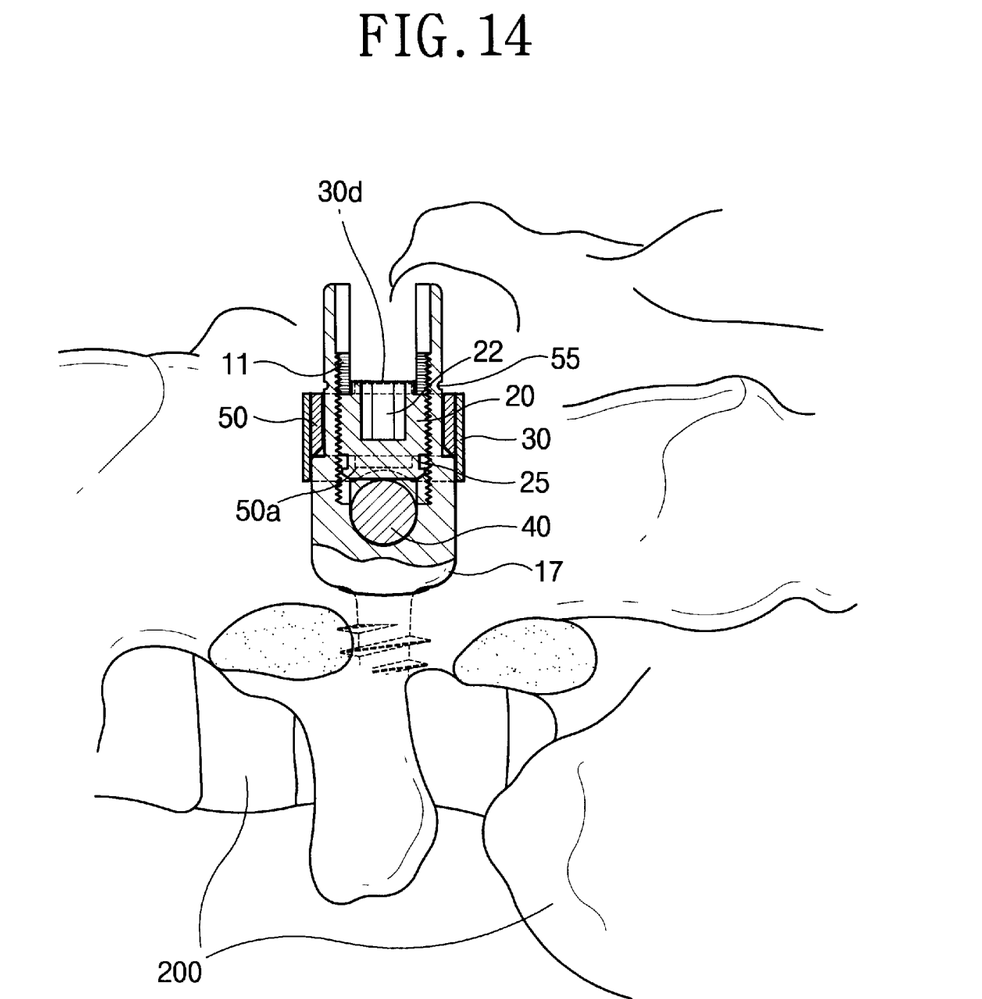
FIG. 14 is a sectional view showing a function of a spine supporting system according to the second embodiment of the present invention.

FIG. 10 is an exploded perspective view showing a structure of a spine supporting system according to the second embodiment of the present invention, FIG. 11 is a sectional view showing a double structure of an outer cap and a reinforcement ring applied to a spine supporting system according to the second embodiment of the present invention, FIG. 12 is an exploded perspective view showing a double structure of an outer cap and a reinforcement ring applied to a spine supporting system according to the second embodiment of the present invention, FIG. 13 is an exploded perspective view showing an example of operation using a spine supporting system according to the second embodiment of the present invention, and FIG. 14 is a sectional view showing a function of a spine supporting system according to the second embodiment of the present invention.

FIG. 10 illustrates the spine support system that is suitable to apply to the patient who needs to reduce the spine to the normal position by a reaction from which the rod 40 connected to the plurality of the spine supporting system is tightened as the inner bolt 20 is joined where a cutting segment 51 is formed at an upper end of the head 12 of the screw 10. This supporting system is applied to the operation, in which restores an abnormal fixed spine 202 to the normal position relatively the spine supporting system, and then cut the unnecessary cutting segment 51 along a cutting line 55, while the rod 40 is forced to be pressed downwardly in the state that the rod 40 is lifted excessively in the groove 16.

In the second embodiment, the same names and reference numerals will be given to the same components of the first embodiment, and in the drawings the numerals will be given to characterized part so as to give the explanation more apparently.

The inner bolt 20 and outer cap 30 are integrated, and a reinforcement ring 50 is joined in the outer cap 30 in the spine supporting system of the second embodiment The inner bolt 20 is formed with a fastening part 23 at the upper part thereof and a fastening groove 25 at the lower part thereof.

The outer cap 30 is formed at the upper part thereof with a supporting segment 30d having a supporting end 30c, which has the curvature corresponding an outer diameter of a fastening part 23 of the inner bolt 20, and is formed with a punching point 30b at the predetermined part of both sides. Also, the lower part of outer cap 30 is formed with a round cut part 30f at a contact part with the rod 40 in the insertion.

The reinforcement ring 50 has an outer diameter to be fitted tightly in an inner diameter of the outer cap, and is formed with a fixing opening 50c fastened at the punching point 30b, at an outer surface corresponding to the punching point 32b of the outer cap 30. In addition, at the lower part thereof, a supporting segment 50a having a supporting end 50b which has the curvature corresponding an outer diameter of the fastening groove 25 of the inner bolt 20, is formed.

In such a structure, the reinforcement ring 50 is inserted in the outer cap 30, and the fastening part 23 and fastening groove 25 of the inner bolt 20 are inserted rotatively in the supporting segment 30d of the outer cap 30 and the supporting segment 50a of the reinforcement ring 50 respectively.

With respect to the function of the second embodiment according to the present invention, the explanation will be given referring FIG. 13 and FIG. 14. The patient, to whom the present embodiment is applied, is in the state that the spine is separated and dislocated from the normal position so that it touches or presses the nerve system. As the cutting segment 51 extending from the upper part of a cap assembled surface 13 in the spine supporting system of the present embodiment, in case of separation of the spine, the rod 40 could be inserted in a groove 16 without any difficulties.

Referring to the FIG. 13, using the spine supporting system (A), (B), (C), a dislocated abnormal spine 202 and an adjacent normal spine 200 are connected with the curved rod 40. In the state that the spine supporting system (C) in the normal spine 200 is fixed, the rod 40 is pressed by joining the inner bolt 20 tightly. The abnormal spine 202 is pulled up and restored to the normal position, as the spine supporting system (A),(B) fixed in the abnormal spine 202 moves up as a reaction. After that, the cutting segment 51 is cut and disposed using a proper operation tool and the cutting line 55.

While the inner bolt 20 is joined by external force capable of restoring the abnormal spine 202 in fastening the inner bolt 20 tightly, the joining is not achieved and the initial centering is not easy, and thereby the operation becomes difficult, since the spine supporting system of the prior art supports the inner bolt 20 only in the lower part as the single outer cap 30. However, since the present invention comprises a double structure of the outer cap and reinforcement ring 30, 50 and supports the upper and lower part of the inner bolt 20 rotatively, only by covering the head 12 with the outer cap 30, the initial centering is achieved easily. Also, since the outer circumference of the head is supported rigidly by the double structure of the outer cap and reinforcement ring 30, 50 in the state that the inner bolt 20 is inserted completely in the head 12, the head part is supported rigidly.

While the application of a rigid screw in which the body 14 and head 12 are integrated is described in the first and second embodiment, the a polyaxial screw in which the body 14 and the head 12 could rotate could be adapted to the present invention, and it is apparent that this falls into the scope of the present invention.

The effects of the present invention could be summarized as follows.

In the present invention, after the small inner bolt is joined with the outer cap preliminarily in the outer circumstance of operation part, the outer cap larger than the inner bolt covers the head of the screw, and then the inner bolt guided by the outer cap is joined with the female thread. Therefore, the initial setting of the inner bolt and the female thread of the head and the insertion of the outer cap and head become very easy. Additionally, in the complete joining of the inner bolt, the inner bolt and the head of the screw is joined, and the seat recess of the outer cap is fastened to the head part of the inner bolt, so that the screw, inner bolt, and outer cap are integrated with each other and exert the rigid fixation. Further, since the lower part of the inner cavity in the outer cap is formed large and main contacting part of the outer cap and head of the screw is round, the outer cap could be inserted in the head without any difficulties. Also, when the outer cap is inserted to the head, the inner bolt is inserted accurately in the female thread of the head automatically only by rotating the inner bolt, so that the rapid and accurate operation could be schemed. Furthermore, since the outer cap covers and supports the entire head part, the fixation is strengthened and the life of the supporting system is extended.

In the spine supporting system which the inner bolt and outer cap is integrated, since the upper and lower part of the inner bolt is supported by the double structure of the outer cap and reinforcement ring, steady and forceful rotation is ensured and the head part is supported rigidly.

Although a number of embodiment have described in the above specification, it should be apparent that the present invention could be embodied in many other specific mode included within the sprit and scope of the present invention. Thus, the present embodiments should be considered as illustrative, and the present invention could be modified within the scope of claims and the equivalent thereof.

What is claimed is:

1. A spine supporting system comprising:
  a screw having a cone shaped body and a head including at least a female thread, cap assembled surface, and a head block;
  an inner bolt having a male thread at an outer circumference to be inserted and mounted in the head of the screw;
  an outer cap having an inner cavity to cover the head of the screw; and a rod inserted in the head of the screw and fixed by the outer cap and the inner bolt, being characterized in that the outer cap is formed with a guide female thread at an upper part of an inner cavity, thereby joining the inner bolt to the guide female thread of the outer cap preliminary, wherein the outer cap guides the inner bolt to the female thread of the screw, and the inner bolt is joined to the female thread of the screw completely after mounting the outer cap to the head of the screw.

2. A spine supporting system comprising:

a screw having a cone shaped body and a head including at least a female thread;

an inner bolt formed with a head part extending outwardly from an upper part thereof, having a male thread at an outer circumference to be inserted and mounted in the head of the screw;

an outer cap having an inner cavity to cover the head of the screw being characterized in that the outer cap is formed with a guide female thread at an upper part of the inner cavity, and the outer cap is formed at an upper part of the guide female thread with a seat recess; and a rod inserted in the head of the screw and fixed by the outer cap and the inner bolt thereby joining the inner bolt to the guide female thread of the outer cap preliminary, wherein the outer cap guides the inner bolt to the female thread of the screw and the inner bolt is joined to the female thread of the screw completely in which the head part of the inner bolt is fastened and seated in the seat recess after mounting the outer cap to the head of the screw.

3. A spine supporting system comprising:

a screw having a cone shaped body and a head including at least a female thread, cap assembled surface, and a head block;

an inner bolt having a male thread at an outer circumference to be inserted and mounted in the head of the screw;

an outer cap having an inner cavity to cover the head of the screw, the inner cavity of the outer cap includes a first and second step surface having different inner diameters in order to cover the cap assembled surface and head block of the head; and a rod inserted in the head of the screw and fixed by the outer cap and the inner bolt, being characterized in that the outer cap is formed with a guide female thread at an upper part of the inner cavity, thereby joining the inner bolt to the guide female thread of the outer cap preliminary, and then joining the inner bolt to the female thread of the screw completely after mounting the outer cap to the head of the screw.

4. A spine supporting system comprising:

a screw having a cone shaped body and a head including at least a female thread;

an inner bolt having a male thread at an outer circumference to be inserted and mounted in the head of the screw;

an outer cap having an inner cavity to cover the head of the screw; and a rod inserted in the head of the screw and fixed by the outer cap and the inner bolt, being characterized in that the outer cap is formed with a guide female thread at an upper part of the inner cavity, thereby joining the inner bolt to the guide female thread of the outer cap preliminary, wherein the guide female thread is formed with a pitch of a limited number of crests and roots, such that the inner bolt is only joined to the outer cap preliminarily and guided thereby such that the centering and joining of the female thread of the screw and the inner bolt, after mounting the outer cap to the head of the screw is not interfered with.

5. A spine supporting system comprising:

a screw having a cone shaped body and a head including at least a female thread, cap assembled surface, and a head block, the screw is formed with a first and second round surface at a boundary of the cap assembled surface and an upper surface and a portion between the cap assembled surface and the head block respectively;

an inner bolt having a male thread at an outer circumference to be inserted and mounted in the head of the screw;

an outer cap having an inner cavity to cover the head of the screw, wherein the outer cap is formed with round surfaces at a portion between a first and second step surface and in an inner end of a lower part in the second step surface respectively; and a rod inserted in the head of the screw and fixed by the outer cap and the inner bolt, being characterized in that the outer cap is formed with a guide female thread at an upper part of an inner cavity, thereby joining the inner bolt to the guide female thread of the outer cap preliminary, and then joining the inner bolt to the female thread of the screw completely after mounting the outer cap to the head of the screw.

6. A spine supporting system comprising:

an inner bolt formed with a respective fastening part of an upper part and fastening groove of the lower part;

an outer cap formed with a supporting segment of an upper part, the supporting segment being joined rotatively with the fastening part of the inner bolt; and a reinforcement ring joined in the outer cap by tight fitting, a supporting segment in a lower part of the reinforcement ring being joined rotatively in the fastening groove of the inner bolt, wherein joining the inner bolt supported at the upper and lower part thereof by the outer cap and reinforcement ring.

* * * * *